United States Patent
Lee et al.

(10) Patent No.: US 7,432,571 B2
(45) Date of Patent: Oct. 7, 2008

(54) MULTI-SCALE CANTILEVER STRUCTURES HAVING NANO SIZED HOLES AND METHOD OF PREPARING THE SAME

(75) Inventors: Jung Hyun Lee, Pohang (KR); Pyung Soo Lee, Pohang (KR); Kun Hong Lee, Pohang (KR); Nayoung Shin, Pohang (KR)

(73) Assignees: Postech Foundation, Pohang (KR); Postech Academy-Industry Foundation, Pohang (KR)

( * ) Notice: Subject to any disclaimer, the term of this patent is extended or adjusted under 35 U.S.C. 154(b) by 55 days.

(21) Appl. No.: 11/553,283

(22) Filed: Oct. 26, 2006

(65) Prior Publication Data

US 2007/0137308 A1 Jun. 21, 2007

(30) Foreign Application Priority Data

Oct. 27, 2005 (KR) ........................ 10-2005-0101748

(51) Int. Cl.
*H01L 31/00* (2006.01)

(52) U.S. Cl. .................. 257/414; 257/415; 257/421; 257/E31.001; 438/50; 438/52

(58) Field of Classification Search ........... 257/414, 257/415, 421, E31.001; 438/50, 52
See application file for complete search history.

(56) References Cited

U.S. PATENT DOCUMENTS

| | | | |
|---|---|---|---|
| 4,624,741 A * | 11/1986 | Daniele | 216/2 |
| 4,783,237 A * | 11/1988 | Aine et al. | |
| 5,265,470 A * | 11/1993 | Kaiser et al. | 73/178 R |
| 5,536,963 A * | 7/1996 | Polla | |
| 5,587,343 A * | 12/1996 | Kano et al. | |
| 5,789,264 A * | 8/1998 | Chung | |
| 5,898,515 A * | 4/1999 | Furlani et al. | |
| 5,914,507 A * | 6/1999 | Polla et al. | 257/254 |
| 5,929,438 A * | 7/1999 | Suzuki et al. | 250/306 |
| 5,998,742 A * | 12/1999 | Liu et al. | 177/210 EM |
| 6,551,849 B1 * | 4/2003 | Kenney | |
| 6,613,241 B1 * | 9/2003 | Scherer et al. | 216/52 |
| 6,753,488 B2 * | 6/2004 | Ono et al. | 200/181 |
| 6,800,503 B2 * | 10/2004 | Kocis et al. | |
| 6,953,977 B2 * | 10/2005 | Mlcak et al. | |
| 6,967,362 B2 * | 11/2005 | Nam et al. | 257/254 |
| 7,172,707 B2 * | 2/2007 | Fork et al. | 216/2 |

(Continued)

OTHER PUBLICATIONS

Cherian et al, "Determination of adsorption-induced variation in the spring constant of a microcantilever," Applied Physics Letters, Mar. 2002, vol. 80, No. 12, pp. 2219-2221.

*Primary Examiner*—Evan Pert
*Assistant Examiner*—Victor A Mandala, Jr.
(74) *Attorney, Agent, or Firm*—Rothwell, Figg, Ernst & Manbeck

(57) ABSTRACT

Provided are a multi-scale cantilever structure having nano-sized holes prepared by anodic oxidation and a method of preparing the same. The multi-scale cantilever structure is prepared using anodic oxidation and electro-polishing so that a manufacturing process is simple and a manufacturing cost is inexpensive. In addition, the multi-scale cantilever structure has a porous structure having a plurality of nano-sized holes inside thereof, and thus a surface area of the cantilever structure can be maximized. Therefore, when the cantilever structure is used in a sensor, the sensor can have improved sensitivity and selectivity.

12 Claims, 9 Drawing Sheets

U.S. PATENT DOCUMENTS

| | | |
|---|---|---|
| 7,172,911 B2* | 2/2007 | Kalvesten et al. |
| 7,253,488 B2* | 8/2007 | Zhan et al. ................. 257/414 |
| 7,351,601 B2* | 4/2008 | Scherer |
| 2002/0135033 A1* | 9/2002 | Hara et al. |
| 2003/0119220 A1* | 6/2003 | Mlcak et al. |
| 2005/0210988 A1* | 9/2005 | Amano et al. ................. 73/704 |
| 2006/0006484 A1* | 1/2006 | Seneviratne et al. |
| 2006/0030066 A1* | 2/2006 | Hantschel et al. |
| 2007/0023851 A1* | 2/2007 | Hartzell et al. .............. 257/414 |
| 2007/0117234 A1* | 5/2007 | Fork et al. |
| 2007/0209437 A1* | 9/2007 | Xue et al. ................ 73/514.31 |
| 2007/0222007 A1* | 9/2007 | Van Beek et al. |

* cited by examiner

MULTI-SCALE CANTILEVER STRUCTURES HAVING NANO SIZED HOLES AND METHOD OF PREPARING THE SAME

CROSS-REFERENCE TO RELATED PATENT APPLICATION

This application claims the benefit of Korean Patent Application No. 10-2005-0101748, filed on Oct. 27, 2005, in the Korean Intellectual Property Office, the disclosure of which is incorporated herein in its entirety by reference.

BACKGROUND OF THE INVENTION

1. Field of the Invention

The present invention relates to a cantilever structure having nano-sized holes and a method of preparing the same, and more particularly, to a porous multi-scale cantilever structure having nano-sized holes prepared using anodic oxidation and electro-polishing and a method of preparing the same.

2. Description of the Related Art

A Conventional system of electrically or optically detecting micro-particles is quartz crystal mass balance (QCM). However, a quartz single crystal of QCM is so fragile that QCM cannot be made to become small and thin and is not suitable for mass-production.

However, small-sized sensors based on a micro electro mechanical system (MEMS) in which electric and mechanical components are recently united to be microminiaturized draw people's attention since the sensors response quickly, have high sensitivity, and are suitable for mass-production.

The MEMS enables the microminiaturized products to be mass-produced at a low cost by applying a microelectronics fabrication in which processes such as deposition, etching, etc. are repeatedly performed. In addition, the MEMS uses a driving force such as coulombic force that is a force between charged particles, a magnetic force, a force by a thermal expansion difference, etc., and the microminiaturized products significantly reduce their power consumption because of their small size. Therefore, the importance of the MEMS is highlighted along with nanotechnique and system on chip (SOC) technique.

In recent days, to detect a physical phenomenon or a chemical reaction, many studies in developing sensors based on MEMS processed cantilevers have been conducted.

FIGS. 1A through 1C are flow charts illustrating a method of preparing such a conventional cantilever structure. First, in FIG. 1A, a sacrificial layer 2 is formed on a substrate 1, and then a pattern is formed on the sacrificial layer 2 using a mask. In FIG. 1B, a material to become a cantilever 3 is deposited on the sacrificial layer 2, and then a pattern of the material to become a cantilever 3 is formed using another mask. Subsequently, when the sacrificial layer 2 is removed, a conventional cantilever structure as in FIG. 1C is formed.

Sensors using a cantilever under study measure static deflection of the cantilever according to mass change, etc. by absorbing heat or gases using a light source such as laser. However, in the case of a conventional sensor using a light source such as laser, the sensor has to have a light source so that decreasing a size of the sensor is limited.

Besides the method of sensing by static deflection by laser, there is a method of sensing using a change in resonance frequency. Thundat, et al of Oak Ridge National Lab confirmed in Applied Physics Letters 80, 2219-2221 (2002) that a spring constant change by $Na^+$ ion absorption on a surface of a micro cantilever due to resonance frequency measurement could be measured. In addition, researchers in IBM Swiss Zurich laboratory reported that the sensing method by resonance frequency measurement could be used for sensing a predetermined gas of air.

However, all the methods described above use a reaction on a surface of the cantilever. Therefore, in order to obtain high sensitivity even at low driving voltage, it is desired that the cantilever has a larger surface area. However, there was a limit on increasing a surface area in a cantilever structure having a constant size. In addition, there is a method of increasing a surface area of a cantilever structure by preparing nanoholes using a lithography method that uses electron beam (E-beam), scanning tunneling microscope (STM), etc. on a surface of the cantilever structure. However, when the method is used, a manufacturing cost is high, a manufacturing process is complicated, and productivity is very limited.

SUMMARY OF THE INVENTION

The present invention provides a multi-scale cantilever structure having nano-sized holes prepared using anodic oxidation and electro-polishing.

The present invention also provides a method of preparing the multi-scale cantilever structure having nano-sized holes.

The objective of the present invention can be all achieved by configuration of the present invention that will be described below.

According to an aspect of the present invention, there is provided a multi-scale cantilever structure comprising: a first layer comprising an aluminum substrate that comprises a first region having a height t1 and a second region having a height t2 that is greater than t1; a second layer that is formed on the first layer, comprising a cantilever that is composed of alumina, wherein the cantilever comprises a main body connected to the second region and a protruding part that protrudes towards the first region from the main body and is separated from a surface of the first region; a third layer that is formed on the second layer, comprising a metal thin film layer; and a fourth layer formed on the third layer.

According to another aspect of the present invention, there is provided a multi-scale cantilever structure comprising: a first layer comprising an aluminum substrate that comprises a first region having a height t1 and a second region having a height t2 that is greater than t1; and a second layer that is formed on the first layer, comprising a cantilever that is composed of alumina, wherein the cantilever comprises a main body connected to a second region of the aluminum substrate, a protruding part that protrudes towards the first region from the main body and is separated from a surface of the first region, and nano-sized holes that are exposed towards the outside.

According to another aspect of the present invention, there is provided a method of preparing a multi-scale cantilever structure comprising: forming an alumina layer having a plurality of nano-sized holes by anodic oxidizing an aluminum substrate; forming a first structure by sequentially depositing a metal thin film layer and a photoresist layer on the alumina layer; forming a photoresist layer pattern having a convex cross section by arranging a mask having a pattern of a convex cross section on the first structure and then exposing the photoresist layer to light and developing the photoresist layer; forming a metal thin film layer pattern having a convex cross section by wet etching the metal thin film layer using the photoresist layer pattern as a mask and a metal etching solution to remove the metal thin film layer on a region that is not covered by the pattern; forming a second structure having a convex cross section by wet etching the alumina layer using the metal thin film layer pattern as a mask and an alumina etching solution to remove the alumina layer that is not covered by the metal thin film layer pattern; and forming a cantilever separated from a surface of the first region of the aluminum substrate by electro-polishing the aluminum substrate to remove, by a surface reaction, a top portion of the aluminum substrate in the first region which is not covered by the second structure.

The term "multi-scale" used in the present invention represents that the cantilever structure according to the present invention has a multi-layered structure.

In a multi-scale cantilever structure and a method of preparing the same according to the present invention, nano-sized holes are formed within the cantilever structure using alumina prepared by anodic oxidation. Unlike a conventional method such as electron-beam lithography, the method according to the present invention does not require a complicated and expensive process. In addition, the cantilever structure includes nano-sized holes so that a surface area of the cantilever structure can be significantly increased. When the cantilever structure is used in a sensor, the sensor can have improved sensitivity and selectivity.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, a multi-scale cantilever structure according to an embodiment of the present invention and a method of preparing the same will be described in detail with reference to the accompanying drawings.

Figure 1A:
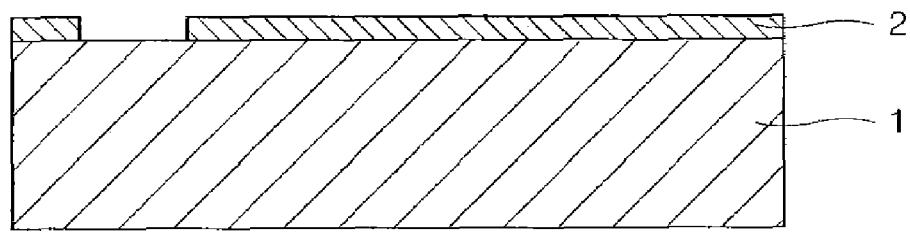
FIGS. 1A through 1C are flow charts illustrating a method of preparing a conventional cantilever structure.
Figure 1B:
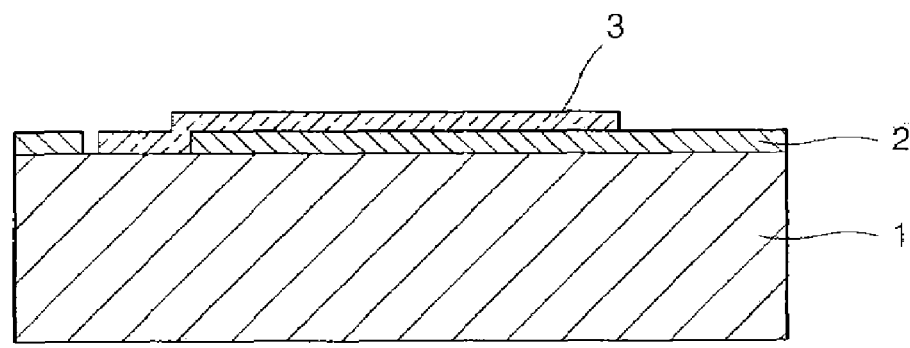
Figure 1C:
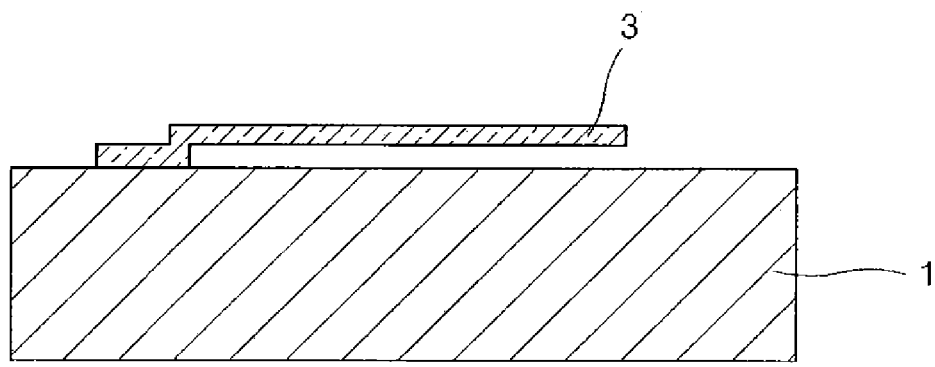
Figure 2:
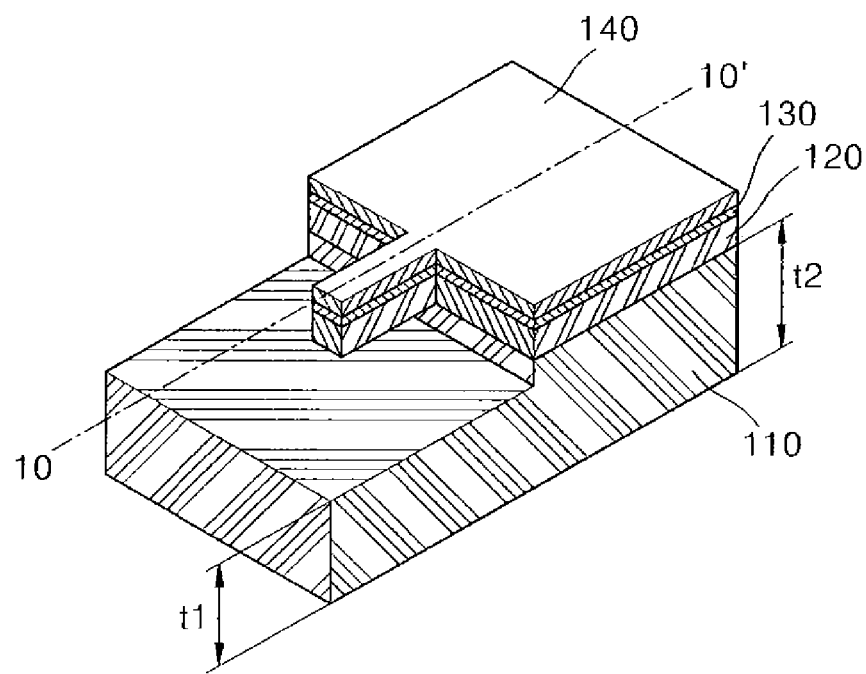
FIG. 2 is a perspective view illustrating a multi-scale cantilever structure according to an embodiment of the present invention.
Figure 3:
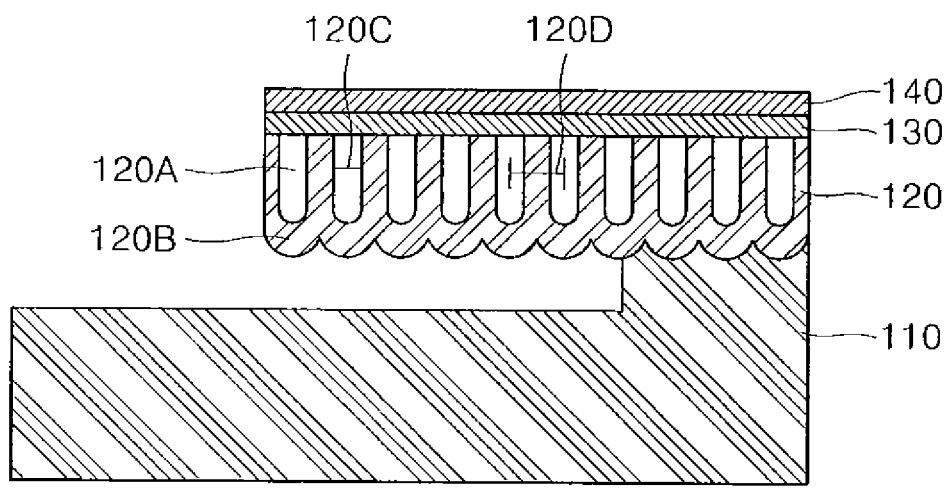
FIG. 3 is a cross-sectional view of a multi-scale cantilever structure taken along a line of 10-10', according to an embodiment of the present invention.

FIG. 2 is a perspective view illustrating a multi-scale cantilever structure according to an embodiment of the present invention, and FIG. 3 is a cross-sectional view of a multi-scale cantilever structure taken along a line of 10-10', according to an embodiment of the present invention.

Referring to FIGS. 2 and 3, a multi-scale cantilever structure according to an embodiment of the present invention comprises: a first layer 110 comprising an aluminum substrate that comprises a first region having a height t1 and a second region having a height t2 that is greater than t1; a second layer 120 that is formed on the first layer, comprising a cantilever that is composed of alumina, wherein the cantilever comprises a main body connected to the second region and a protruding part that protrudes towards the first region from the main body and is separated from a surface of the first region; a third layer 130 that is formed on the second layer, comprising a metal thin film layer; and a fourth layer 140 formed on the third layer.

In the multi-scale cantilever structure according to the current embodiment of the present invention, it is desirable that the fourth layer 140 is a photoresist layer in order to be easily converted to another structure by etching.

In addition, in the multi-scale cantilever structure, the fourth layer can be a nanobead layer, a cavitand receptor layer, a thin polymeric film layer, a metal oxide thin film layer, an organism receptor layer or a self-assembly monolayer (SAM). In the multi-scale cantilever structure that uses the materials as the fourth layer, the cantilever can have improved response speed and selectivity.

In the current embodiment, the cantilever 120 is composed of alumina, and nano-sized holes that are integrated in a high density are formed inside of the cantilever 120. A diameter 120C of the nano-sized hole formed in the cantilever 120, a distance 120D between the nano-sized holes and the number of the nano-sized holes per unit area can be easily adjusted by a kind of electrolyte, a temperature of electrolyte, applied voltage, etc in a process of anodic oxidation. In addition, a thickness of the cantilever 120 can be controlled by time in which voltage is applied, etc. in a process of anodic oxidation.

Figure 4:
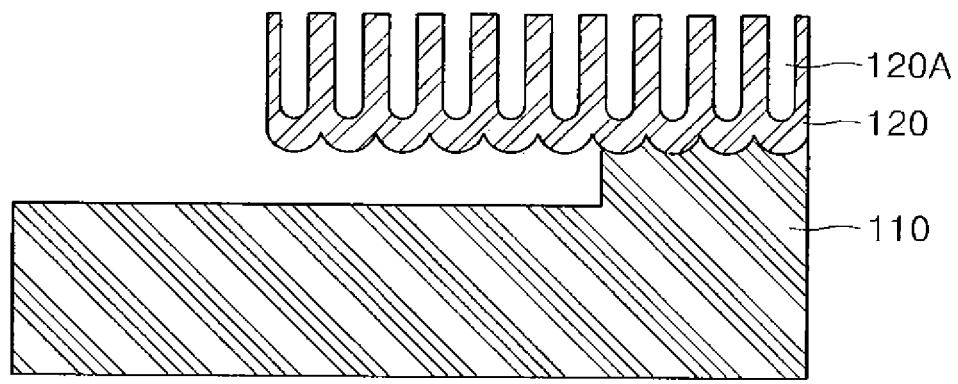
FIGS. 4 through 6 are cross-sectional views of multi-scale cantilever structures taken along a line of 10-10', according to embodiments of the present invention.

FIG. 4 is a cross-sectional view of a multi-scale cantilever structure according to another embodiment of the present invention.

Referring to FIG. 4, the multi-scale cantilever structure according to the current embodiment of the present invention is a cantilever composed of a first region having a height t1 and alumina formed on the aluminum substrate, and comprises a main body connected to a second region of the aluminum substrate, a protruding part that protrudes towards the first region from the main body and is separated from a surface of the first region, and a second layer with a plurality of nano-sized holes that are exposed towards the outside.

The multi-scale cantilever structure according to another embodiment of the present invention illustrated in FIG. 4 does not include the metal thin film layer and the fourth layer of the multi-scale cantilever structure according to an embodiment of the present invention illustrated in FIG. 3.

The metal thin film layer 130 formed on the cantilever 120 and the fourth layer 140 formed on the metal thin film layer 130 protect the cantilever 120 when a height difference between t1 and t2 is formed in the aluminum substrate 110 through electro-polishing. Therefore, in general, when the metal thin film layer 130 and the fourth layer 140 are removed, it is preferable that the metal thin film layer 130 and the fourth layer 140 are lastly removed in order to minimize damage applied to the cantilever 120.

In the current embodiment of the present invention, when the metal thin film layer 130 is removed after the cantilever 120 is formed, the cantilever 120 may be damaged. So in order to minimize damage of the cantilever 120 in the process of removing the metal thin film layer, an alumina layer is etched in the process of preparing the second structure and then the fourth layer 140 is removed using an organic solvent such as acetone. Then, wet etching is performed to remove the metal thin film layer 130 in advance. Thereafter, electro-polishing is performed to form the cantilever 120 of which nano-sized holes are exposed.

Figure 5:
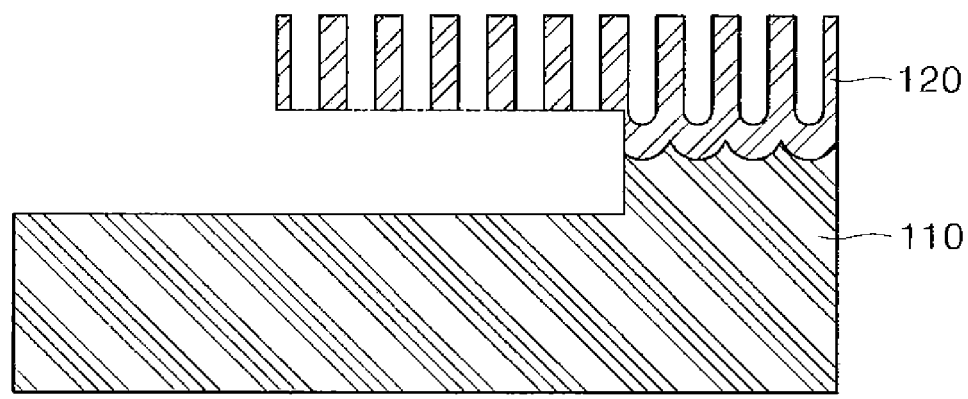

FIG. 5 is a cross-sectional view of a multi-scale cantilever structure according to an embodiment of the present invention.

Referring to FIG. 5, an aluminum substrate is anodic oxidized to form alumina, and then barrier 120B is made to become thinner through voltage drop, etc. Then, subsequent processes are performed to form a second structure, remove the fourth layer 140 and metal thin film layer 130 and form a cantilever structure. Thereafter, the thinned barrier 120B is removed by wet etching to form a multi-scale cantilever structure having a membrane structure as in FIG. 5. The multi-scale cantilever structure having the membrane structure has a more increased surface area so that the cantilever can have more improved response speed and selectivity.

Figure 6:
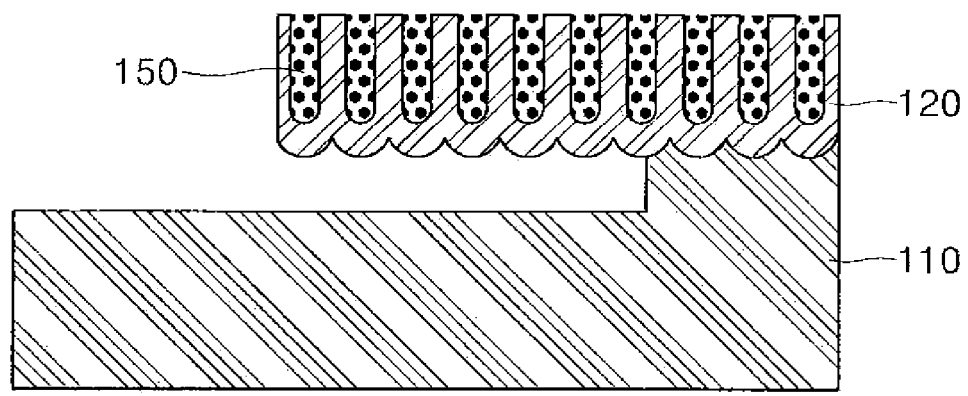

FIG. 6 is a cross-sectional view of a multi-scale cantilever structure according to an embodiment of the present invention.

Referring to FIG. 6, the multi-scale cantilever structure according to the current embodiment of the present invention can further include a predetermined material 150 that fills nano-sized holes of the cantilever 120. The predetermined material can be metal, metal oxide, conductive polymer, a magnetic material, a piezoelectric material, a fluorescent material, a light emitting material, a carbon nanotube (CNT), nanowire, DNA or a stem cell. In FIG. 6, the multi-scale cantilever structure from which the metal thin film layer 130 and the fourth layer 140 are removed is illustrated. However, nano-sized holes of the multi-scale cantilever structure from which the metal thin film layer 130 and the fourth layer 140 are not removed can be filled with the predetermined material 150.

In the current embodiment of the present invention, the nano-sized holes formed within the alumina generally have a well-arranged hexagonal structure. However, if another well-arranged structure besides the hexagonal structure is needed, the nano-sized holes can have another shape such as round, triangle or rectangle. The nano-sized holes having such another shape can be formed by making a dent in a desired shape using a nano indentor before anodic oxidation is performed and then performing anodic oxidation to form alumina.

FIGS. 7A through 7F are flow charts illustrating a method of preparing a multi-scale cantilever structure according to an embodiment of the present invention.

Referring to FIGS. 7A through 7F, a method of preparing the multi-scale cantilever structure according to the current embodiment of the present invention includes: forming an alumina layer having a plurality of nano-sized holes by anodic oxidizing an aluminum substrate; forming a first structure by sequentially depositing a metal thin film layer and a photoresist layer on the alumina layer; forming a photoresist layer pattern having a convex cross section by arranging a mask having a pattern of a convex cross section on the first structure and then exposing the photoresist layer to light and developing the photoresist layer; forming a metal thin film layer pattern having a convex cross section by wet etching the metal thin film layer using the photoresist layer pattern as a mask and a metal etching solution to remove the metal thin film layer on a region that is not covered by the pattern; forming a second structure having a convex cross section by wet etching the alumina layer using the metal thin film layer pattern as a mask and an alumina etching solution to remove the alumina layer that is not covered by the metal thin film layer pattern; and forming a cantilever separated from a surface of the first region of the aluminum substrate by electro-polishing the aluminum substrate to remove, by a surface reaction, a top portion of the aluminum substrate in the first region which is not covered by the second structure.

Hereinafter, a method of preparing the multi-scale cantilever structure will be described in great detail with reference to FIGS. 7A through 7F.

Figure 7A:
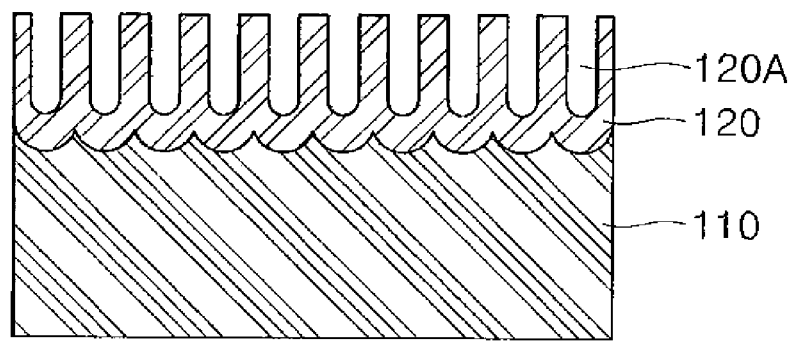
FIGS. 7A through 7F are flow charts illustrating a method of preparing a multi-scale cantilever structure according to an embodiment of the present invention.

First, FIG. 7A illustrates a method of forming an alumina layer 120 having a plurality of nano-sized holes 120A by anodic oxidizing an aluminum substrate 110. Here, a method of preparing the alumina layer 120 by anodic oxidation and a method of preparing nano-sized holes in the alumina layer will be described in more detail. First, electro-polishing is performed to remove roughness of a surface of the aluminum substrate 110. Then, the aluminum substrate 110 is set as an anode in an aqueous electrolyte solution of a phosphoric acid, an oxalic acid, a sulfuric acid, a sulfonic acid or a chromic acid, and then about 1-200 V direct voltage is applied to the anode to convert the aluminum substrate 110 to an alumina layer 120 including holes having a nano-sized diameter. A degree at which the aluminum substrate is converted to the alumina layer is proportional to time of anodic oxidation. For example, when anodic oxidation is performed under conditions of a reaction temperature of 15° C., a voltage of 40 V, and 0.3 M of an aqueous oxalic acid solution, the aluminum substrate is converted to the alumina layer by a thickness of about 1 μm per 10 minutes.

The nano-sized holes that are formed on the alumina layer 120 by anodic oxidation can have a hexagonal shape. In addition, the nano-sized holes having such a round, triangular, rectangular shape, etc. can be formed by making a dent in a desired shape using a nano indentor before anodic oxidation is performed and then performing anodic oxidation to form alumina.

A diameter 120C of the nano-sized hole, a distance 120D between the nano-sized holes and the number of the nano-sized holes per unit area can be easily adjusted by applied voltage, a kind of electrolyte, a concentration of electrolyte, a temperature of electrolyte, etc in a process of anodic oxidation. For example, when anodic oxidation is performed under conditions of a voltage of 25 V, a reaction temperature of 10° C., and 0.3 M of an aqueous sulfuric acid solution, the formed nano-sized hole has a diameter 121C of about 20 nm, and a distance 120D between nano-sized holes is about 60 nm. When anodic oxidation is performed under conditions of a voltage of 40 V, a reaction temperature of 15° C., and 0.3 M of an aqueous oxalic acid solution, the formed nano-sized hole has a diameter 120C of about 40 nm, and a distance 120 D between nano-sized holes is about 100 nm. When anodic oxidation is performed under conditions of a voltage of 160 V, a reaction temperature of 0° C., and 0.3 M of an aqueous phosphoric acid solution, the formed nano-sized hole has a diameter 120C of about 100 nm, and a distance 120 D between nano-sized holes is about 450 nm. The number of the nano-sized holes formed per unit area can be generally about $10^8 \sim 10^{11}$ numbers/cm$^2$, and the number depends on applied voltage. A diameter 120C of the nano-sized hole that can be formed by anodic oxidation is about 4-300 nm. The diameter 120C of the nano-sized hole can be controlled by a chemical post-treatment using a phosphoric acid, sodium hydroxide or the like without a change in the number of nano-sized holes formed per unit area.

Figure 7B:
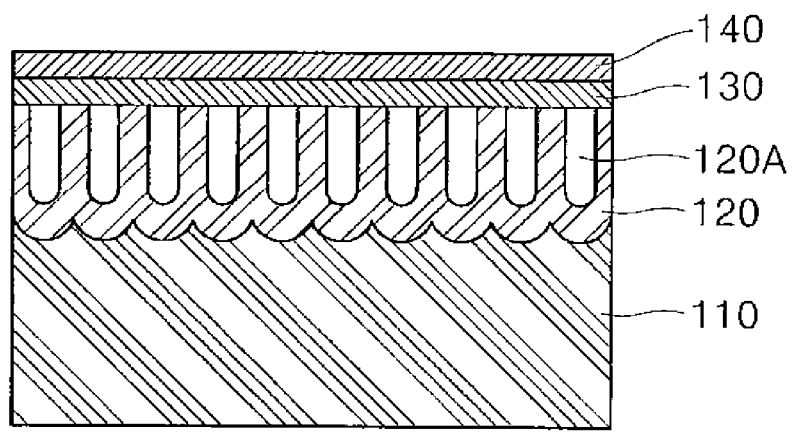

FIG. 7B illustrates a method of forming a first structure by sequentially depositing a metal thin film layer and a photoresist layer on the alumina layer. Here, the term "first structure" denotes a four-layered structure in a process before etching is performed.

Referring to 7B, the metal thin film layer 130 is deposited on the alumina layer 120 that is formed by anodic oxidation using sputtering or electron beam deposition, and then the photoresist layer 140 is formed on the deposited metal thin film layer 130 using spin coating. Here, it is desirable that the metal thin film layer is an aluminum thin film layer.

Figure 7C:
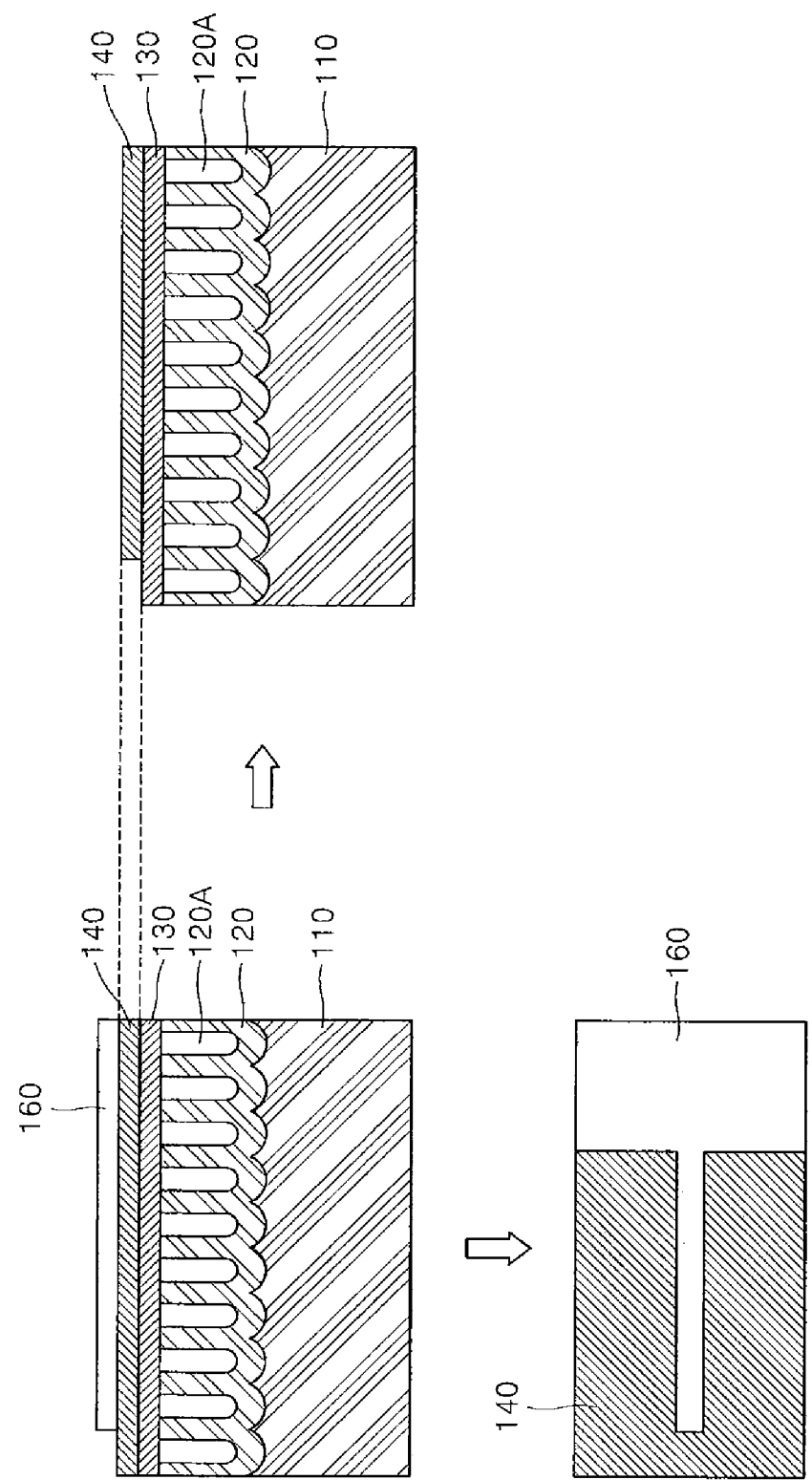

FIG. 7C illustrates a method of forming a photoresist layer having a pattern of the convex cross section by arranging a mask having a pattern of a convex cross section on the first structure and then exposing the mask to light and developing the mask.

Referring to FIG. 7C, first, a mask 160 having the convex pattern is mounted on the photoresist layer 140, and then the photoresist layer 140 is exposed to light to etch a portion of the photoresist layer which is not covered by the mask. Then, when the mask is removed, the photoresist layer 140 having a pattern of a convex cross section can be developed as FIG. 7B. In FIG. 7C, a right drawing illustrates a cross-sectional view of a structure after the photoresist layer is etched and the mask is removed, and a below drawing illustrates a plane view of a structure of when the mask is deposited on the photoresist layer 140 before the photoresist layer 140 is etched. As can be seen in the below drawing of FIG. 7C, when the etching of the photoresist layer and removal of the mask are terminated, the photoresist layer 140 having a pattern of a convex cross section is formed on the top portion.

Figure 7D:
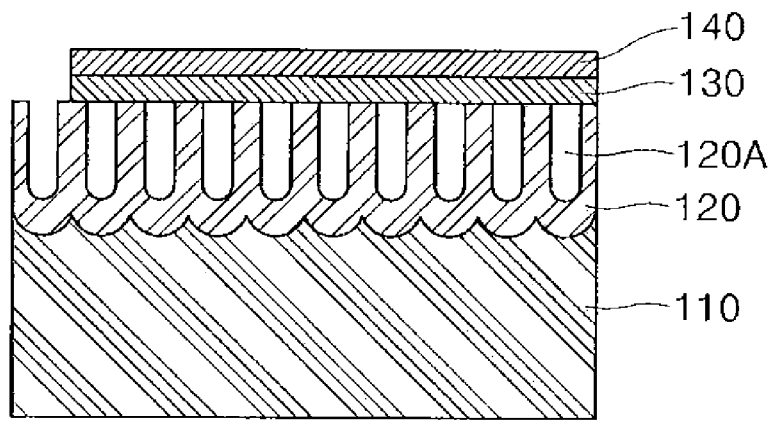

FIG. 7D illustrates a method of forming a metal thin film layer having a pattern of a convex cross section by wet etching the metal thin film layer using the photoresist layer pattern as a mask and a metal etching solution to remove a portion of the metal thin film layer that is not covered by the photoresist layer pattern.

Referring to FIG. 7D, an outside portion of the pattern of the photoresist layer 140 having a convex shape is etched by applying an etching solution that can etch metal on a structure including the photoresist layer pattern. In the current embodiment of the present invention, when the metal thin film layer is an aluminum thin film layer, it is desirable that the etching solution is an aluminum etching solution. For example, a solution comprising $H_3PO_4$, $H_2O$, $CH_3COOH$ and $HNO_3$ in a mass ratio of 16:2:1:1 can be used as the etching solution. The aluminum thin film layer etching can be performed by immersing the structure according to the current embodiment of the present invention into the etching solution at a room temperature, stirring the immersed structure for twenty minutes to remove the aluminum layer 130, and transferring the pattern developed on the photoresist layer 140 to the aluminum layer. However, the aluminum etching solution can also etch the alumina layer 120. Therefore, when the structure is immersed in the aluminum etching solution for a long time, the alumina layer 120 that forms a cantilever is also etched so that a cantilever with a desired shape cannot be formed. Accordingly, the structure has to be immersed in the etching solution for a predetermined time.

Figure 7E:
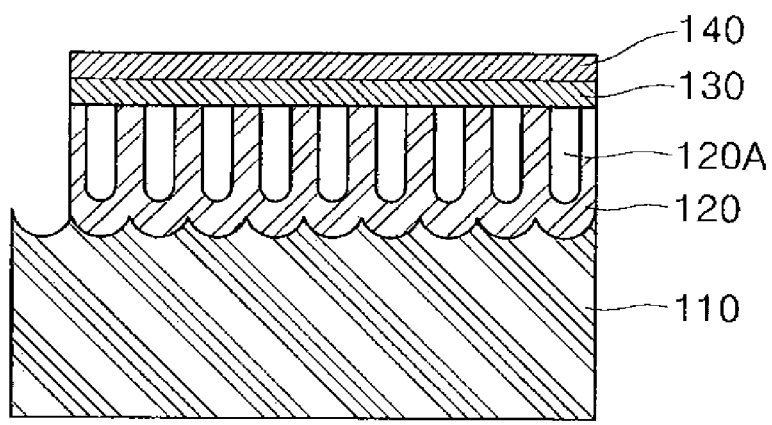

FIG. 7E illustrates a method of forming a second structure having a convex cross section by wet etching the alumina layer using the metal thin film layer pattern as a mask and an alumina etching solution to remove a portion of the alumina layer that is not covered by the metal thin film layer pattern.

Referring to FIG. 7E, wet etching is performed using the metal thin film layer 130 formed in FIG. 7D as a mask and an alumina etching solution. The alumina etching solution used in the current embodiment of the present invention is 5 weight % of a $H_3PO_4$ solution and can be used at a room temperature. The alumina layer 120 is immersed into the solution and stirred to be etched. As a result, a second structure having a convex shape is formed. At this time, a stirring time is determined by a thickness of the alumina layer 120. Here, the 'second structure' is a four-layered structure in a process before the aluminum substrate is etched by electro-polishing, and denotes a structure having a convex shape.

The method of preparing the multi-scale cantilever structure having nano-sized holes according to an embodiment of the present invention can further comprise exposing nano-sized holes of the cantilever 120 towards the outside. The nano-sized holes of the cantilever 120 is exposed towards the outside by removing the photoresist layer 140 using an organic solvent such as acetone after the second structure having a convex shape is formed, and removing the metal thin film layer 130 by wet etching.

Figure 7F:
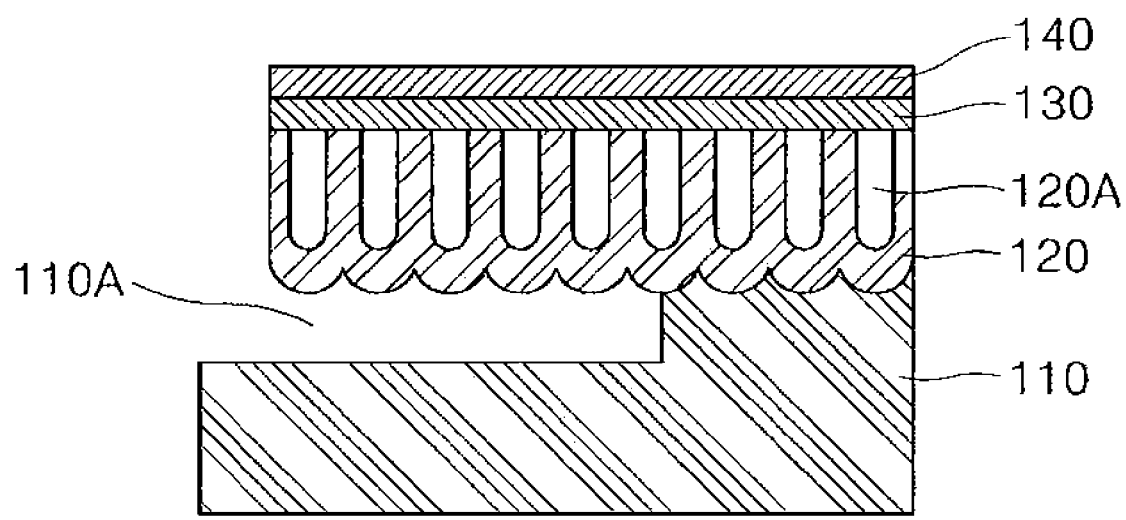

FIG. 7F illustrates a method of forming a cantilever separated from a surface of the first region of the aluminum substrate by electro-polishing the aluminum substrate to remove a top portion of the aluminum substrate on the first region which is not covered by the second structure by a surface reaction.

Referring to FIG. 7F, aluminum in the first region which is disposed below the alumina layer 120 of the second structure is removed by electro-polishing to complete a structure having a cantilever of which one end is separated from the first region of the aluminum substrate. When electro-polishing is performed using an etching solution that can etch both aluminum and alumina, a cantilever structure having a desired shape cannot be formed. Therefore, it is desirable that an etching solution that can selectively etch only aluminum is used. In the current embodiment of the present invention, it is desirable that the aluminum etching solution is a solution comprising perchloric acid and ethanol in a volume ratio of 1:4, and electro-polishing can be performed using the aluminum etching solution at 5° C. and a voltage of 20 V. Here, the 'electro-polishing' is to etch the aluminum substrate by immersing the first region of the aluminum substrate into the aluminum etching solution, and then applying positive voltage to the aluminum substrate and applying negative voltage to platinum or a carbon electrode so that aluminum metal ions are ionized from the aluminum substrate. An electro-polishing time depends on a required width of the cantilever.

To form a cantilever having a membrane structure after the cantilever is formed according to the method of the present invention, a method of removing the photoresist layer 140 and the metal thin film layer 130 can be further included after the second structure having a convex cross section is formed. In addition, a method of removing a barrier layer can be further included by wet etching a lower portion of the alumina after the cantilever is formed.

In the current embodiment, the cantilever 120 having a multi-scale cantilever structure formed by the above process includes nano-sized holes that are integrated in a high density inside of the cantilever 120.

In addition, the method of preparing the multi-scale cantilever structure can further include removing the photoresist layer 140 after the cantilever is formed and forming a nano-bead layer, a cavitand receptor layer, a thin polymeric film layer, a metal oxide thin film layer, an organism receptor layer or a self-assembly monolayer (SAM) on the metal thin film layer 130. The multi-scale cantilever structure including the material layer formed by the above process can have more improved response speed or selectivity.

In addition, in the current embodiment of the present invention, when a method of forming and removing the metal thin film layer 130 and the photoresist layer 140 after the nano-sized holes within the alumina are filled with the predetermined material 150 is repeatedly performed after the aluminum substrate is formed, a cantilever structure including the predetermined material within the nano-sized holes can be prepared. Here, the predetermined material can be metal, metal oxide, conductive polymer, a magnetic material, a piezoelectric material, a fluorescent material, a light emitting material, a carbon nanotube (CNT), nanowire, DNA or a stem cell.

Figure 8:
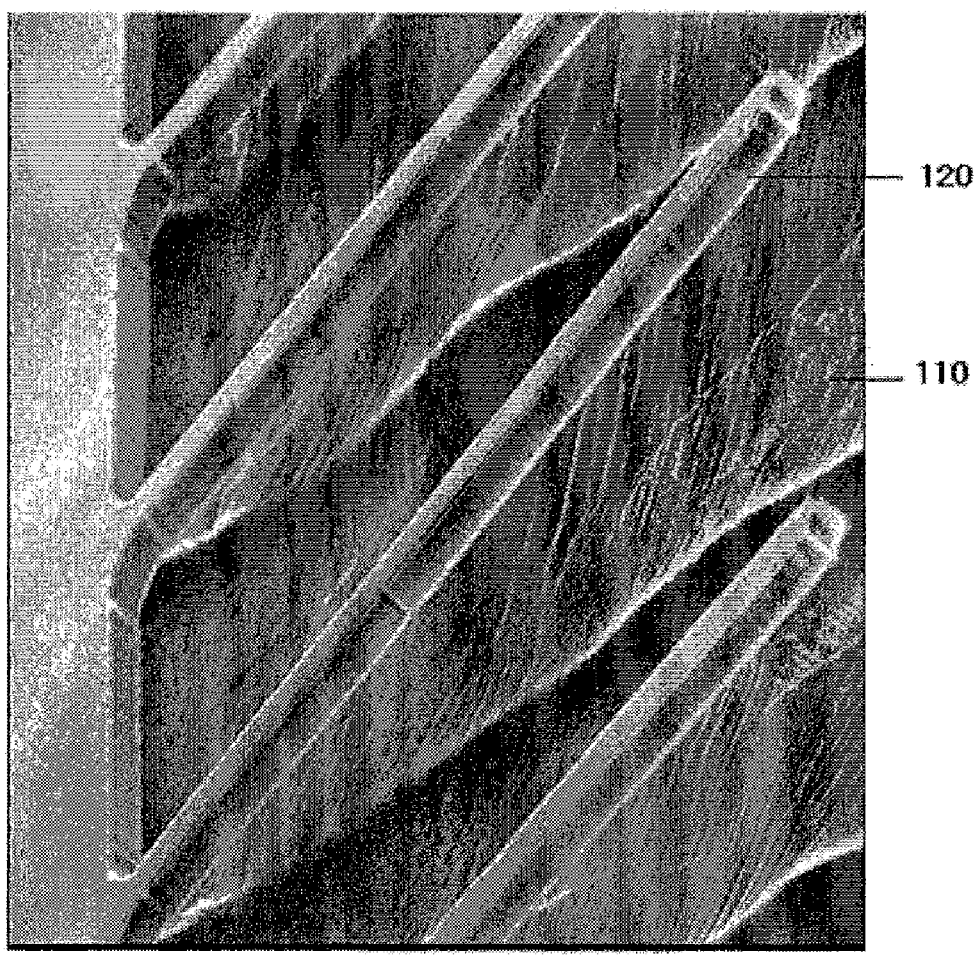
FIG. 8 is a SEM image of a multi-scale cantilever structure prepared according to an embodiment of the present invention.

FIG. 8 is a SEM image of a multi-scale cantilever structure prepared according to an embodiment of the present invention. As can be seen in FIG. 8, the prepared cantilever structure includes a cantilever of which one end is separated from a surface of the aluminum substrate, since the aluminum substrate that is disposed below the cantilever is removed.

The multi-scale cantilever structure according to the present invention has a plurality of nano-sized holes within alumina prepared by anodic oxidation. Therefore, a complicated and expensive process required for increasing a surface area as in the prior art is not required, and a surface area of the cantilever structure can be significantly increased.

Therefore, when the multi-scale cantilever structure according to the present invention and the method of preparing the same are used, a precise sensor of which sensitivity and selectivity are improved can be simply obtained.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A multi-scale cantilever structure comprising:
a first layer comprising an aluminum substrate that comprises a first region having a height t1 and a second region having a height t2 that is greater than t1;
a second layer that is formed on the first layer, comprising a cantilever that is composed of alumina, wherein the cantilever comprises a main body connected to the second region and a protruding part that protrudes towards the first region from the main body and is separated from a surface of the first region;
a third layer that is formed on the second layer, comprising a metal thin film layer; and
a fourth layer formed on the third layer.

2. The multi-scale cantilever structure of claim 1, wherein the fourth layer is a photoresist layer.

3. The multi-scale cantilever structure of claim 1, wherein the fourth layer is a nanobead layer, a cavitand receptor layer, a thin polymeric film layer, a metal oxide thin film layer, an organism receptor layer or a self-assembly monolayer (SAM).

4. The multi-scale cantilever structure of claim 1, wherein the cantilever is a porous structure having nano-sized holes.

5. The multi-scale cantilever structure of claim 1, wherein the cantilever is a membrane structure, excluding a barrier layer on its lower portion.

6. The multi-scale cantilever structure of claim 4, wherein the nano-sized holes are filled with a predetermined material.

7. The multi-scale cantilever structure of claim 6, wherein the predetermined material is metal, metal oxide, conductive polymer, a magnetic material, a piezoelectric material, a fluorescent material, a light emitting material, a carbon nanotube (CNT), nanowire, DNA or a stem cell.

8. The multi-scale cantilever structure of claim 4, wherein the nano-sized holes have a hexagonal cross section.

9. The multi-scale cantilever structure of claim 4, wherein the nano-sized holes have a round, triangular or rectangular cross section.

10. The multi-scale cantilever structure of claim 1, wherein the metal thin film layer is an aluminum thin film layer.

11. A multi-scale cantilever structure comprising:
a first layer comprising an aluminum substrate that comprises a first region having a height t1 and a second region having a height t2 that is greater than t1; and
a second layer that is formed on the first layer, comprising a cantilever that is composed of alumina, wherein the cantilever comprises a main body connected to a second region of the aluminum substrate, a protruding part that protrudes towards the first region from the main body and is separated from a surface of the first region, and nano-sized holes that are exposed towards the outside.

12. The multi-scale cantilever structure of claim 11, wherein the cantilever is a porous structure having nano-sized holes.

* * * * *